United States Patent
Liu

(10) Patent No.: US 10,824,225 B2
(45) Date of Patent: Nov. 3, 2020

(54) METHODS AND APPARATUSES FOR DETERMINING HEAD MOVEMENT

(71) Applicant: BEIJING ZHIGU RUI TUO TECH CO., LTD., Beijing (CN)

(72) Inventor: Hao Liu, Beijing (CN)

(73) Assignee: BEIJING ZHIGU RUI TUO TECH CO., LTD., Beijing (CN)

( * ) Notice: Subject to any disclaimer, the term of this patent is extended or adjusted under 35 U.S.C. 154(b) by 261 days.

(21) Appl. No.: 15/544,733

(22) PCT Filed: Jan. 7, 2016

(86) PCT No.: PCT/CN2016/070348
§ 371 (c)(1),
(2) Date: Jul. 19, 2017

(87) PCT Pub. No.: WO2016/115982
PCT Pub. Date: Jul. 28, 2016

(65) Prior Publication Data
US 2018/0011532 A1    Jan. 11, 2018

(30) Foreign Application Priority Data

Jan. 23, 2015 (CN) .................... 2015 1 0035315.4

(51) Int. Cl.
*G06F 3/01* (2006.01)
*A61B 5/00* (2006.01)
(Continued)

(52) U.S. Cl.
CPC ............ *G06F 3/012* (2013.01); *A61B 5/7246* (2013.01); *G06F 3/015* (2013.01); *A61B 5/0476* (2013.01); *A61B 5/11* (2013.01)

(58) Field of Classification Search
CPC ..... G06F 3/012; A61B 5/7246; A61B 5/0476; A61B 5/11
(Continued)

(56) References Cited

U.S. PATENT DOCUMENTS 4,092,981 A * 6/1978 Ertl .................... A61B 5/04014
600/544
7,123,955 B1   10/2006 Xiaorong et al.
(Continued)

FOREIGN PATENT DOCUMENTS

CN    1248426 A    3/2000
CN    2888524 Y    4/2007
(Continued)

OTHER PUBLICATIONS

International Search Report and Written Opinion for Application No. PCT/CN2016/070348, dated Mar. 24, 2016, 10 pages.

*Primary Examiner* — Vernal U Brown
(74) *Attorney, Agent, or Firm* — Sheppard Mullin Richter & Hampton LLP

(57) ABSTRACT

The present application discloses various methods and apparatuses for determining a head movement, wherein a method for determining a head movement disclosed comprises: acquiring, in response to a head movement of a human body, brain electricity detection information of a human body; and determining the head movement corresponding to the brain electricity detection information. The present application provides a new solution for head movement recognition, by which accuracy of head movement recognition is improved.

17 Claims, 4 Drawing Sheets

(51) Int. Cl.
*A61B 5/0476* (2006.01)
*A61B 5/11* (2006.01)

(58) Field of Classification Search
USPC .......................................................... 340/4.1
See application file for complete search history.

(56) References Cited

U.S. PATENT DOCUMENTS

| | | | | |
|---|---|---|---|---|
| 2014/0023999 | A1* | 1/2014 | Greder | A61B 5/0482 |
| | | | | 434/236 |
| 2015/0003651 | A1* | 1/2015 | Han | H04R 1/1041 |
| | | | | 381/312 |
| 2015/0059086 | A1* | 3/2015 | Clough | G08C 17/02 |
| | | | | 5/83.1 |
| 2016/0135726 | A1* | 5/2016 | Zhang | A61B 5/0075 |
| | | | | 600/473 |
| 2017/0340261 | A1* | 11/2017 | Torres | A61B 5/1101 |

FOREIGN PATENT DOCUMENTS

| | | |
|---|---|---|
| CN | 102945078 A | 2/2013 |
| CN | 103150007 A | 6/2013 |
| CN | 103617362 A | 3/2014 |
| CN | 104095648 A | 10/2014 |
| CN | 104267808 A | 1/2015 |
| CN | 104503592 A | 4/2015 |
| CN | 104503593 A | 4/2015 |

\* cited by examiner

METHODS AND APPARATUSES FOR DETERMINING HEAD MOVEMENT

CROSS-REFERENCE TO RELATED APPLICATIONS

This application is a National Phase Application of International Application No. PCT/CN2016/070348, filed on Jan. 7, 2016, which claims priority to and benefit of Chinese Patent Application No. 201510035315.4, filed on Jan. 23, 2015, and entitled "Methods and Apparatuses for Determining Head Movement". Both of the above-referenced applications are incorporated into the present application by reference in their entirety.

TECHNICAL FIELD

The present application generally relates to the field of brain electricity technologies, and in particular, to various methods and apparatuses for determining a head movement.

BACKGROUND

Brain electricity is a human body spontaneous electric discharge activity collected on brain cortex of a human body. It is a relatively stable and objective physiological activity indicator. Currently, applications and researches regarding brain electric signals have inspired wide interests in the industry, for example, in the field of human-computer interaction technologies, an analysis is performed on a brain electric signal of a user while the user is performing motor imagery, so as to identify the intent of the user, and thereby implementing, according to the intent, control of a target object and the like. In addition, in other fields such as medical science and psychology, researches on brain electric signals are conducted continuously to satisfy diversified actual application requirements.

SUMMARY

A brief outline of the present application is given hereinafter to provide a basic understanding of some aspects of the present application. It should be understood that the outline is not an exhaustive one of the present application. It is neither intended to define a key part or an important part of the present application nor intended to limit the scope of the present application. The objective thereof is only giving some concepts in simplified forms and using these concepts as a preface for a more detailed description discussed later.

Embodiments of the present application provide various methods and apparatuses for determining a head movement.

In one aspect, an embodiment of the present application provides a method for determining a head movement, comprising:

acquiring, in response to a head movement of a human body, brain electricity detection information of the human body; and determining the head movement corresponding to the brain electricity detection information.

In the other aspect, an embodiment of the present application further provides an apparatus for determining a head movement, comprising:

a brain electricity detection information acquiring module, configured to acquire, in response to a head movement of a human body, brain electricity detection information of the human body; and a head movement determining module, configured to determine the head movement corresponding to the brain electricity detection information.

In the technical solutions provided in the embodiments of the present application, when a human body performs a head movement, brain electricity detection information of the human body may be acquired, and based on the brain electricity detection information, the head movement of the human body is identified, so that a new solution of head movement recognition is provided. Because a brain electricity detection signal used for determining a head movement is characterized by a relatively high amplitude, an distinct waveform characteristic, and the like, in the embodiments of the present application, the brain electricity detection signal is used to recognize the head movement of the human body, so that accuracy of head movement recognition is relatively high.

These and other advantages of the present application will be more apparent through the following detailed description of optional embodiments of the present application with reference to the accompanying drawings.

BRIEF DESCRIPTION OF THE DRAWINGS

The present application may be better understood with reference to the following description given in combination with the accompanying drawings, in which same or similar reference numerals are used to represent same or similar components. The accompany drawings and the following detailed description are both comprised in the specification and form a part of the specification and are further used to exemplify optional embodiments of the present application and explain the principle and advantages of the present application. In the accompany drawings.

Figure 1:
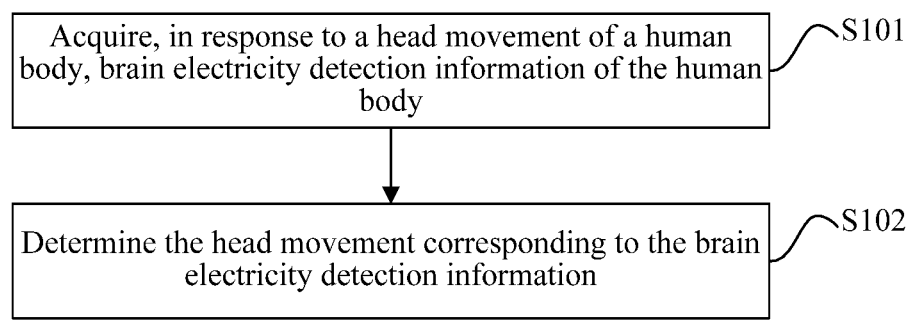
FIG. 1 is a flowchart of a method for determining a head movement according to an embodiment of the present application.

A person skilled in the art should understand that elements in the accompany drawings are shown merely for simplicity and clarity, and may not necessarily drawn in scale. For example, some elements in the drawings may be enlarged in size as compared with other elements to facilitate understanding of the embodiments of the present application.

DETAILED DESCRIPTION

Illustrative embodiments of the present application are described in detail in combination with the accompanying drawings in the following. For clarity and simplicity, not all features of actual implementation manners are described in detail in the specification. However, it should be understood that many decisions specific to actual embodiments must be made in a process of developing any such actual embodiments to achieve a specific objective of a developer, such as compliance with those restrictions related to a particular system and a service, and these restrictions may change depending on different implementation manners. In addition, it should also be understood that although the developing work may be very complex and time consuming, a person skilled in the art will likely benefit from the disclosure in actual implementation.

Here, it should also be noted that, to avoid the present application from being blurred by unnecessary details, in the accompanying drawings and description, only apparatus structures and/or processing steps closely related to the solutions according to the present application are described, and the representation and description that has little association with the present application and for the components and processing known by a person of ordinary skill in the art are omitted.

Specific implementation manners of the present application are further described in detail below with reference to the accompanying drawings (in which same elements are denoted by same reference numerals) and embodiments. The following embodiments are intended to describe the present application, but not to limit the scope of the present application.

A person skilled in the art may understand that the terms such as "first", "second", and the like in the present application are only used to differentiate different steps, devices, modules, or the like, and represent neither any specific technical meaning nor a certain logic sequence between them.

FIG. 1 is a flowchart of a method for determining a head movement according to an embodiment of the present application. The method for determining a head movement provided in the present application is executed by an apparatus for determining a head movement. Device representation forms of the apparatus for determining a head movement are very flexible, for example, the apparatus for determining a head movement may be an independent component, or the apparatus for determining a head movement may be integrated into an electronic device as a functional module, wherein the electronic device may comprise, but is not limited to, a wearable device. Specifically, as shown in FIG. 1, a method for determining a head movement according to an embodiment of the present application comprises:

S101: Acquire, in response to a head movement of a human body, brain electricity detection information of the human body.

S102: Determine the head movement corresponding to the brain electricity detection information.

The head movements may comprise, but is not limited to, nodding, tilting sideways, tilting up, shaking and/or rotating the head of the human body. The foregoing head movements may be spontaneous reactions performed by the human body subconsciously, or may be performed in a specific manner by the human body autonomously, wherein the specific manner may comprise, but is not limited to, time duration, a number of repetitions, and the like of a movement or a combination of several movements.

The inventor of the present application finds that, movements such as nodding, shaking, tilting sideways by the head of a human body cause a physical change inside the head of the human body, and impedance between the skin of the head that is in contact with an electroencephalogram (EEG) sensor element correspondingly changes. These changes reflect that the detected brain electricity information shows a specific characteristic that is different from that when the head of the human body is in a static state (when the head of the human body does not perform the foregoing head movements). Accordingly, in an actual application, when a human body performs a head movement, brain electricity detection information of the human body may be acquired, and based on the brain electricity detection information, the head movement of the human body is identified, so that a new solution of head movement recognition is provided. Because a brain electricity detection signal used for determining a head movement is characterized by a relatively high amplitude, an distinct waveform characteristic, and the like, in the embodiments of the present application, the brain electricity detection signal is used to identify the head movement of the human body, so that accuracy of head movement recognition is relatively high.

A result of identifying a head movement of a human body based on brain electricity detection information is widely applied. For example, in the field of human-computer interaction technologies, a determined head movement may be used as a basis of applications such as subsequent human-computer interaction, for example, as input information of subsequent human-computer interaction control, thereby implementing a natural, flexible, and convenient interaction manner based on head movement control, satisfying diversified actual application requirements of users, and improving user experience; for another example, in the medical science field, for example, a head movement situation of a patient of a specific disease such as Parkinson can reflect, to a certain extent, an illness state, so that recognition may be performed on the head movement of the patient, and illness state monitoring is performed according to a result of the head movement recognition; for still another example, in the nursing field, monitoring and cluster analysis may be performed according to a head movement situation of a rehabilitation training person, and a result thereof is used as a basis for evaluating the rehabilitation training result and the like, and the examples are too numerous to enumerate.

In the technical solution provided in the embodiments of the present application, a manner of determining the head movement corresponding to the brain electricity detection information may be determined according to an actual requirement and can be implemented in a flexible manner.

In a possible implementation manner, a mapping relationship (referred to as a first mapping relationship) between brain electricity information and the head movement may be acquired in advance, and the head movement corresponding to the brain electricity detection information is determined according to the first mapping relationship. The brain electricity information in the first mapping relationship is brain electricity information detected when the human body performs a head movement, and the brain electricity information in the first mapping relationship is a whole of normal brain electricity information of the human body regardless of whether the head of the human body performs the foregoing head movements and an "interference or noise" signal introduced into the normal brain electricity information of the human body due to the foregoing head movements performed by the human body. This solution can identify a head movement according to overall brain electricity detection information corresponding to the head movement.

The first mapping relationship may be acquired in advance, and a means of acquiring the first mapping relationship is very flexible. For example, an apparatus for determining a head movement may acquire the first mapping relationship from an external device (such as a server, a cloud, and an intelligent terminal). Alternatively, for another example, the apparatus for determining a head movement itself may establish the first mapping relationship, for example, the apparatus for determining a head movement establishes the first mapping relationship according to training data. Specifically, when a human body performs different head movements, respective brain electricity information may be detected respectively, and by using a certain amount of learning and training data, specific brain electricity information corresponding to each head movement of the human body is determined, so that the first mapping relationship is established. Brain electricity information of different human bodies may be different. In an actual application, learning and training may be performed for different human bodies, and a learning result is associated with user information of a corresponding human body, so that different learning results are applied for different human bodies. In an actual application process, when the head of a human body performs a head movement, a brain electricity signal thereof is detected to acquire a brain electricity detection signal, matching is performed between the brain electricity detection signal and each piece of brain electricity information in a learning and training database that corresponds to the human body, and the head movement corresponding to the brain electricity information that is matched with the brain electricity detection signal is determined as the head movement corresponding to the brain electricity detection information. This solution can establish the first mapping relationship in a manner such as based on cluster detected learning and training data of brain electricity information of head movements of human bodies, so as to acquire individualized data of brain electricity information reflected when different human bodies perform head movements, so that accuracy of subsequent head movement recognition is improved.

In another optional implementation manner, brain electricity characteristic information of the brain electricity detection information relative to a piece of brain electricity reference information of the human body may be determined; and a head movement corresponding to the brain electricity characteristic information is determined. A brain electricity detection signal acquired in response to a head movement of the human body is represented as a detected EEG, which is a whole comprising brain electricity information of the human body regardless of whether the human body performs the foregoing head movements, and further comprising an "interference or noise" signal introduced into the normal brain electricity information of the human body due to the foregoing head movements performed by the human body. In this solution, the whole of brain electricity detection information is not used as a basis for determining a head movement, rather, the "interference or noise" information relative to the normal brain electricity information of the human body in the whole brain electricity detection information is used as brain electricity characteristic information associated with the head movement, and the brain electricity characteristic information is used as the basis for determining the head movement, and thereby reducing the amount of data that needs to be processed, reducing complexity of data processing, and improving efficiency and accuracy of head movement recognition.

Optionally, the normal brain electricity information of the human body regardless of whether the foregoing head movements are performed may be used as the piece of brain electricity reference information. To extract the brain electricity characteristic information corresponding to the head movement, brain electricity of the same human body acquired when the head of the human body is in a static state may be used as the piece of brain electricity reference information. In an actual application, a piece of brain electricity detection information acquired in response to a head movement of a human body may be compared with the piece of brain electricity reference information, and a part of the brain electricity detection information that is different from the piece of brain electricity reference information is used as the brain electricity characteristic information, wherein the brain electricity characteristic information is equivalent to "interference or noise" information introduced due to the head movement performed by the human body, and the head movement corresponding to the brain electricity characteristic information is determined.

Figure 2A:
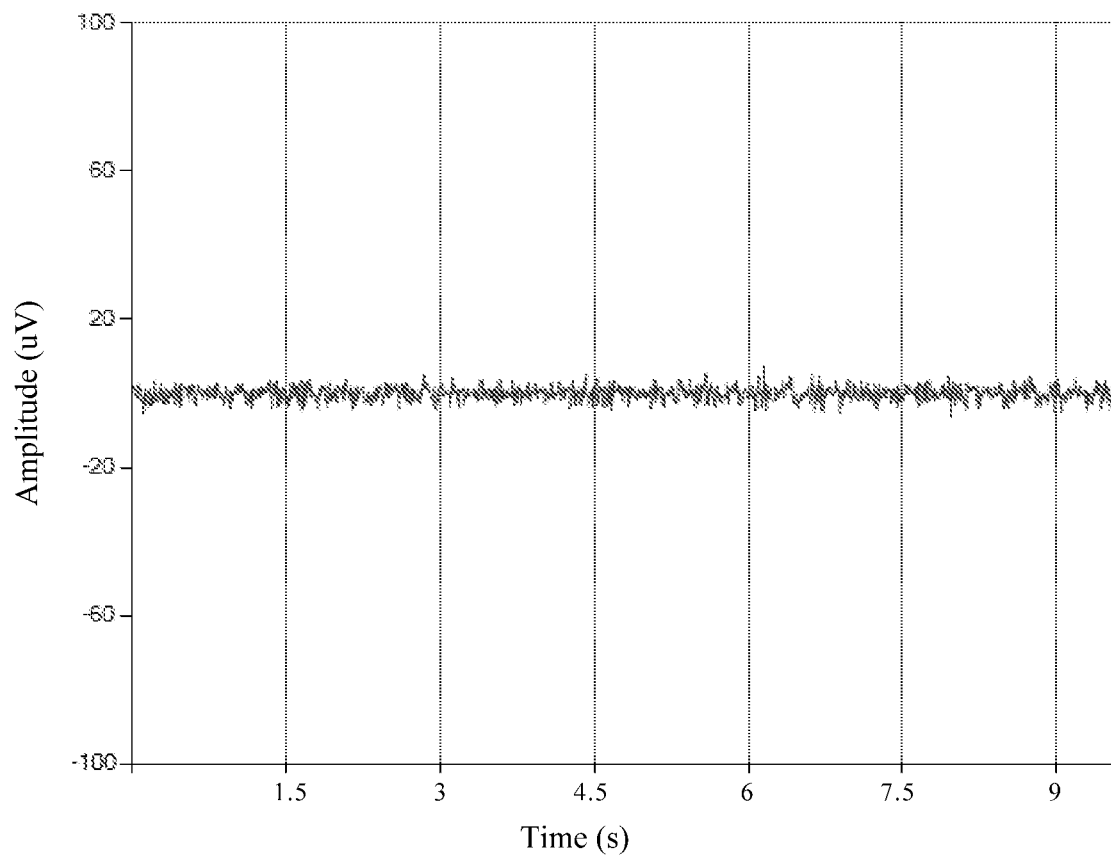
FIG. 2a is an EEG waveform of a human body detected when the head of the human body is in a static state in an optional instance of the present application.
Figure 2B:
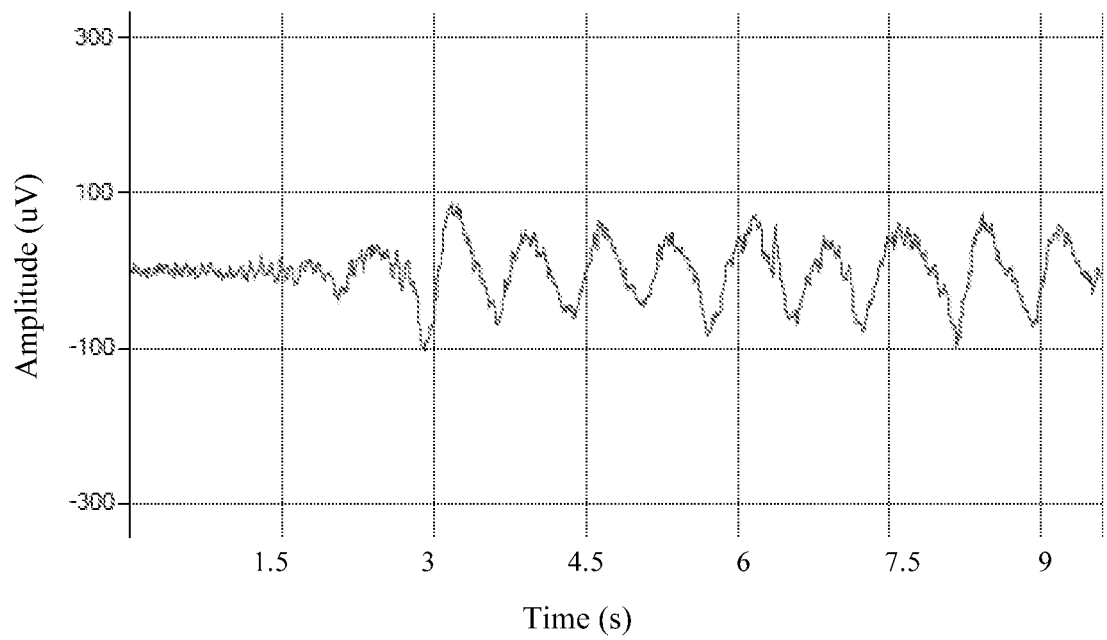
FIG. 2b is an EEG waveform of a human body detected when the human body nods the head in an optional instance of the present application.
Figure 2C:
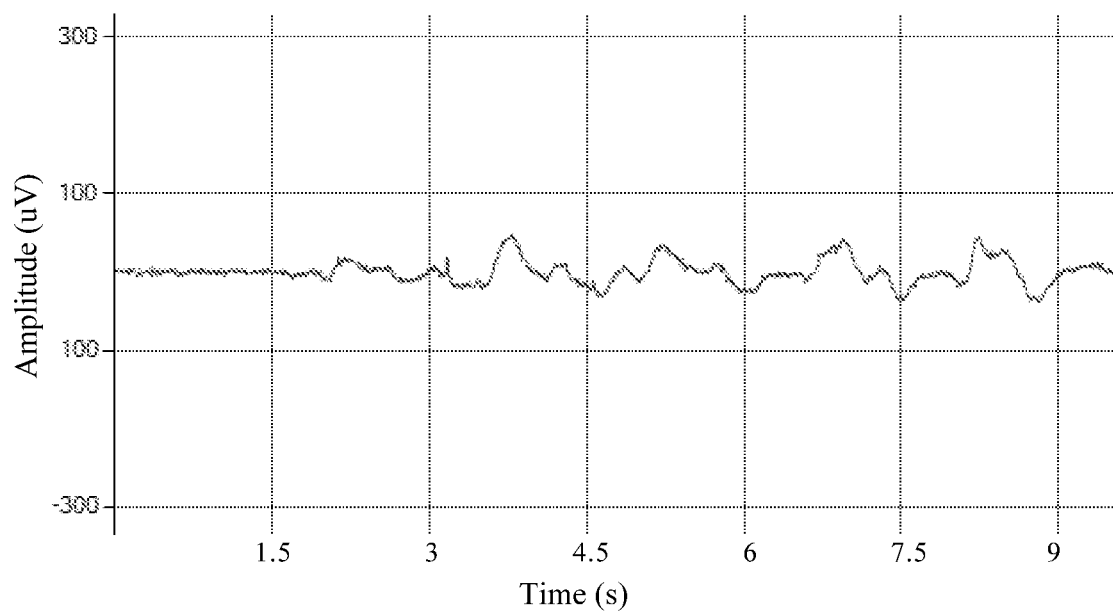
FIG. 2c is an EEG waveform of a human body detected when the human body shakes the head in an optional instance of the present application.

Optionally, the brain electricity characteristic information is determined in a flexible manner, for example, determining the brain electricity characteristic information comprises: extracting information of a frequency band from the brain electricity detection information as brain electricity sample information; and determining, according to an amplitude of the brain electricity sample information and a reference amplitude of the piece of brain electricity reference information in the frequency band, the brain electricity characteristic information. A frequency range of brain electricity information is usually 0 to 32 Hz. During a process of practicing some embodiments of the present application, the inventor of the present application finds that, by comparing brain electricity reference information acquired when the head of a human body is in a static state with brain electricity detection information when the human body performs a head movement, an amplitude in a frequency band within the foregoing frequency range greatly changes, and in the frequency band, an amplitude of the brain electricity detection information is several times or even dozens of times of an amplitude of the brain electricity reference information. For example, when the head of a human body is in a static state, a reference amplitude of brain electricity reference information is usually 0 to 10 uV. As shown in FIG. 2a, amplitudes in some frequency bands of brain electricity detection information when the human body performs a head movement are little different from the brain electricity reference information; however, maximum amplitudes in some frequency bands may reach nearly a hundred uV and are equivalent to dozens of times of reference amplitudes in corresponding frequency bands of the brain electricity reference information. For optional examples, reference may be made to FIG. 2b and FIG. 2c. FIG. 2b is an EEG waveform of a human body detected when the human body nods the head in an optional instance of the present application, and FIG. 2c is an EEG waveform of a human body detected when the human body shakes the head in an optional instance of the present application. Therefore, the frequency band in which the amplitude greatly changes may be extracted as brain electricity sample information. Based on reference amplitudes in corresponding frequency bands of the brain electricity sample information and the brain electricity reference information, the brain electricity characteristic information is determined.

During a process of practicing some embodiments of the present application, the inventor of the present application finds that, in a frequency band of 0 to 5 Hz of brain electricity information of a human body, a difference between brain electricity waves, acquired when the head of the human body perform a movement and the head of the human body is in a static state, is maximum. As shown in FIG. 2b to FIG. 2c, a brain electricity sample signal may be extracted from a frequency band of 0 to 5 Hz, so that brain electricity characteristic information whose amplitude is relatively large may be acquired, and thereby facilitating detection and analysis, and minimizing error. For an optional application example, for example, a difference between an amplitude of the brain electricity sample information in a preset frequency band (for example, 0 to 5 Hz) and a reference amplitude (for example, an average amplitude) of the brain electricity reference information in the corresponding frequency band (0 to 5 Hz) may be calculated, and the difference is used as brain electricity characteristic information corresponding to the head movement. This solution is used to determine brain electricity characteristic information, which facilitates detection, and complexity of data processing is relatively low.

In the technical solution provided in the embodiments of the present application, a manner of determining the head movement corresponding to the brain electricity characteristic information may be determined according to an actual requirement and is implemented in a flexible manner. For example, the head movement corresponding to the brain electricity characteristic information may be determined according to a mapping relationship (referred to as a second mapping relationship) between the brain electricity characteristic information and the head movement. The second mapping relationship may be acquired in advance, and a means of acquiring the second mapping relationship is very flexible. For example, an apparatus for determining a head movement may acquire the second mapping relationship from an external device (such as a server, a cloud, and an intelligent terminal). Alternatively, for another example, the apparatus for determining a head movement itself may establish the second mapping relationship. This solution can identify the head movement according to a part of information, that is, the brain electricity characteristic information corresponding to the head movement in the brain electricity detection information.

Specifically, brain electricity information when the head of the human body is in the static state may be detected as the brain electricity reference information, and when the human body performs different head movements, respective brain electricity information is cluster detected respectively, the detected brain electricity information is compared with the brain electricity reference information, and a frequency band in which an amplitude difference between the detected brain electricity information and the brain electricity reference information is relatively large is determined, for example, a 0 to 5 Hz frequency band, and an average amplitude of the brain electricity reference information in the 0 to 5 Hz frequency band is determined, and then a difference between an amplitude of brain electricity information corresponding to each type of head movement in the 0 to 5 Hz frequency band and the average amplitude of the brain electricity reference information in the 0 to 5 Hz frequency band in a test is calculated, and the difference is used as sample data of brain electricity characteristic information indicating a head movement, and a second mapping relationship between the brain electricity characteristic information and the head movement based on the sample data is established. This solution can establish the second mapping relationship in a manner such as based on cluster detected learning and training data of brain electricity information of head movements of human bodies, so as to acquire individualized characteristic data of brain electricity information reflected when different human bodies perform head movements, and a head movement is identified accordingly.

This solution has advantages such as easy-to-detect, low complexity of data processing, relatively high recognition accuracy, robust, and the like.

Further optionally, before the extracting information of a frequency band from the brain electricity detection information as brain electricity sample information, the method for determining a head movement further comprises: determining that an amplitude of the brain electricity detection information in the frequency band is greater than a preset threshold. The present threshold may be determined according to a characteristic of the brain electricity information caused by the head movement. In this solution, a preset threshold of an amplitude of the brain electricity detection information in a frequency band (for example, 0-5 Hz) may be used as a filtering criterion, so that interference may be reduced to a certain extent.

In addition, any method for determining a head movement provided in the embodiments of the present application may further comprises: acquiring a control instruction corresponding to a determined head movement. Further, the method for determining a head movement may comprise: performing a control operation corresponding to the control instruction. A mapping relationship (referred to as a third mapping relationship) between the head movement and the control instruction may be acquired in advance, and after the head movement corresponding to the brain electricity detection information is determined, a control instruction corresponding to the determined head movement is acquired according to the third mapping relationship, and a control operation corresponding to the control instruction is performed. For example, the determined head movement corresponding to the brain electricity detection information is "nodding", the control instruction corresponding to "nodding" is determined as "Yes" according to the third mapping relationship, so that an electronic device is controlled to perform an operation such as confirmation or selection of a program. For another example, the determined head movement corresponding to the brain electricity detection information is "head shaking", the control instruction corresponding to "head shaking" is determined as "No" according to the third mapping relationship, so that an electronic device is controlled to perform an operation such as cancellation or deletion of a program. For still another example, the determined head movement corresponding to the brain electricity detection information is "tilting the head to the right side", the control instruction corresponding to "tilting the head to the right side" is determined as "increasing the volume" according to the third mapping relationship, so that a playback device is controlled to perform an operation such as increasing the volume. The third mapping relationship may be acquired from an external device, or may be established by the apparatus for determining a head movement itself, and the embodiments of the present application is not limited thereto. This solution can perform natural, flexible, and convenient interaction based on a head movement identified by using brain electricity information, satisfy diversified actual application requirements of users, and improve user experience.

A person skilled in the art may understand that, in any of the foregoing methods of the specific implementation manners of the present application, the value of the serial number of each step does not mean an execution sequence, and the execution sequence of each step should be determined according to the function and internal logic thereof, and should not be any limitation to the implementation procedure of the specific implementation manners of the present application.

Figure 3:
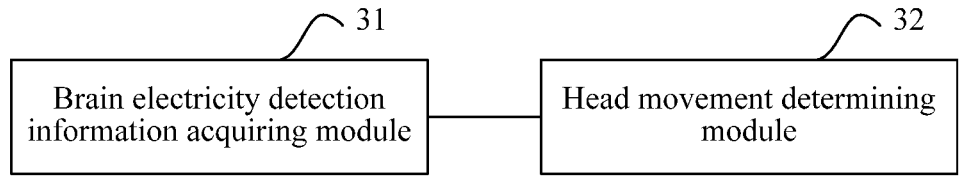
FIG. 3 is a logic block diagram of an apparatus for determining a head movement according to an embodiment of the present application.

FIG. 3 is a logic block diagram of an apparatus for determining a head movement according to an embodiment of the present application. As shown in FIG. 3, an embodiment of the present invention provides an apparatus for determining a head movement, comprising a brain electricity detection information acquiring module 31 and a head movement determining module 32.

The brain electricity detection information acquiring module 31 is configured to acquire, in response to a head movement of a human body, brain electricity detection information of the human body.

The head movement determining module 32 is configured to determine the head movement corresponding to the brain electricity detection information.

Device representation forms of the apparatus for determining a head movement provided in the embodiments of the present application are very flexible, for example, the apparatus for determining a head movement may be an independent component, or the apparatus for determining a head movement may be integrated into an electronic device as a functional module, wherein the electronic device may comprise, but is not limited to, a wearable device.

The apparatus for determining a head movement may acquire, when a human body performs a head movement, brain electricity detection information of the human body, and based on the brain electricity detection information, the head movement of the human body is identified, so that a new solution of head movement recognition is provided. Because a brain electricity detection signal used for determining a head movement is characterized by a relatively high amplitude, an distinct waveform characteristic, and the like, in the embodiment of the present application, the brain electricity detection signal is used to identify the head movement of the human body, so that accuracy of head movement recognition is relatively high.

Figure 4:
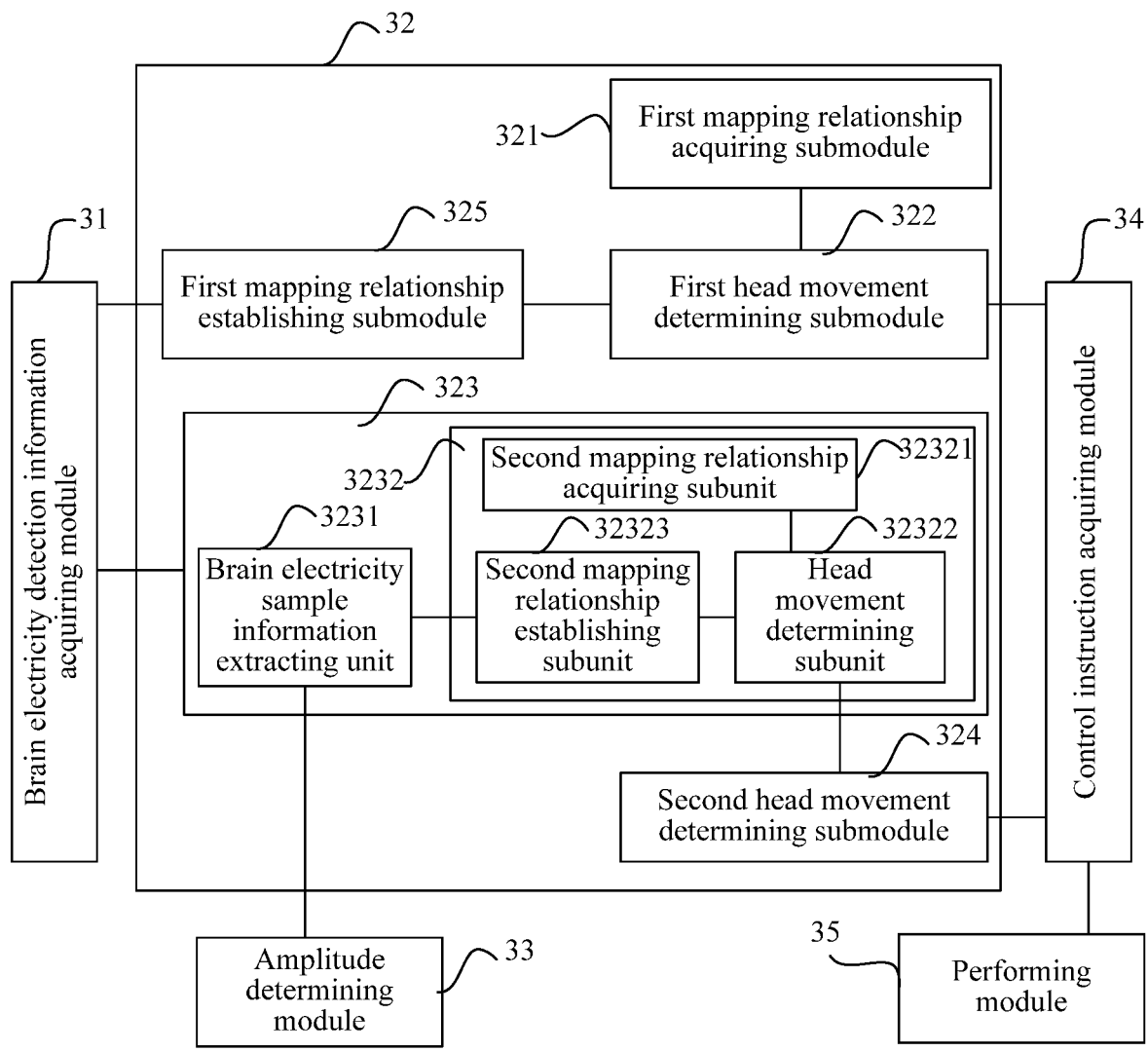
FIG. 4 is a logic block diagram of another apparatus for determining a head movement according to an embodiment of the present application.

Optionally, as shown in FIG. 4, the head movement determining module 32 comprises: a first mapping relationship acquiring submodule 321 and a first head movement determining submodule 322, or the head movement determining module 32 comprises: a first mapping relationship establishing submodule 325 and a first head movement determining submodule 322. The first mapping relationship acquiring submodule 321 is configured to acquire a first mapping relationship between brain electricity information and the head movement; and the first head movement determining submodule 322 is configured to determining the head movement corresponding to the brain electricity detection information. This solution can identify a head movement according to whole brain electricity detection information corresponding to the head movement.

The first mapping relationship establishing submodule 325 is configured to establish a first mapping relationship; and the first head movement determining submodule 322 is configured to determine the head movement corresponding to the brain electricity detection information according to the first mapping relationship. This solution can establish the first mapping relationship based on cluster detected learning and training data of brain electricity information of head movements of human bodies, so as to acquire individualized data of brain electricity information reflected when different human bodies perform head movements, so that accuracy of subsequent head movement recognition is improved.

Alternatively, optionally, the head movement determining module 32 comprises: a brain electricity characteristic information determining submodule 323 and a second head movement determining submodule 324. The brain electricity characteristic information determining submodule 323 is configured to determine brain electricity characteristic information of the brain electricity detection information relative to a piece of brain electricity reference information of the human body; and the second head movement determining submodule 324 is configured to determine the head movement corresponding to the brain electricity characteristic information. This solution can reduce the amount of data that needs to be processed, reduce complexity of data processing, and improve efficiency and accuracy of head movement recognition.

Optionally, the piece of brain electricity reference information is brain electricity information of the human body acquired when the head of the human body is in a static state. This solution facilitates extracting brain electricity characteristic information corresponding to a head movement.

Optionally, the brain electricity characteristic information determining submodule 323 comprises: a brain electricity sample information extracting unit 3231 and a brain electricity characteristic information determining unit 3232. The brain electricity sample information extracting unit 3231 is configured to extract information of a frequency band from the brain electricity detection information as brain electricity sample information; and the brain electricity characteristic information determining unit 3232 is configured to determine, according to an amplitude of the brain electricity sample information and a reference amplitude of the piece of brain electricity reference information in the frequency band, the brain electricity characteristic information. Optionally, the frequency band is 0 to 5 Hz. This solution may be used to determine brain electricity characteristic information, which facilitates detection, and complexity of data processing is relatively low.

Optionally, the apparatus for determining a head movement further comprises: an amplitude determining module 33. The amplitude determining module 33 is configured to determine that an amplitude of the brain electricity detection information in the frequency band is greater than a preset threshold and enable, according to a determined result, the brain electricity sample information extracting unit. In this solution, a preset threshold of an amplitude of the brain electricity detection information in a frequency band (for example, 0-5 Hz) is used as a filtering criterion, so that interference may be reduced to a certain extent.

Optionally, the brain electricity characteristic information determining unit 3232 comprises: a second mapping relationship acquiring subunit 32321 and a head movement determining subunit 32322, or the brain electricity characteristic information determining unit 3232 comprises: a second mapping relationship establishing subunit 32323 and the head movement determining subunit 32322.

The second mapping relationship acquiring subunit 32321 is configured to acquire a second mapping relationship between the brain electricity characteristic information and the head movement; and the head movement determining subunit 32322 is configured to determine, according to the second mapping relationship, the head movement corresponding to the brain electricity characteristic information. This solution can identify a head movement according to a part of information corresponding to the head movement in brain electricity detection information.

The first mapping relationship establishing submodule 32323 is configured to establish a second mapping relationship; and the head movement determining submodule 32322 is configured to determine the head movement corresponding to the brain electricity characteristic information according to the second mapping relationship. This solution can establish the second mapping relationship based on cluster detected learning and training data of brain electricity information of head movements of human bodies, so as to acquire individualized data of brain electricity information reflected when different human bodies perform head movements, so that accuracy of subsequent head movement recognition is improved.

Optionally, the head movement comprises: nodding, tilting sideways, tilting up, shaking and/or rotating by the head of the human body. The foregoing head movements may be spontaneous reactions performed by the human body subconsciously, or may be performed in a specified manner by the human body autonomously, wherein the specified manner may comprise, but is not limited to, time duration, a quantity of repetitions, and the like of a movement or a combination of several movements.

Optionally, the apparatus for determining a head movement may further comprise: a control instruction acquiring module 34, wherein the control instruction acquiring module 34 is configured to acquire a control instruction corresponding to the determined head movement. Further optionally, the apparatus for determining a head movement may further comprise: a performing module 35, wherein the performing module 35 is configured to perform a control operation corresponding to the control instruction. This solution can implement a natural, flexible, and convenient interaction manner based on head movement control, satisfy diversified actual application requirements of users, and improve user experience.

Figure 5:
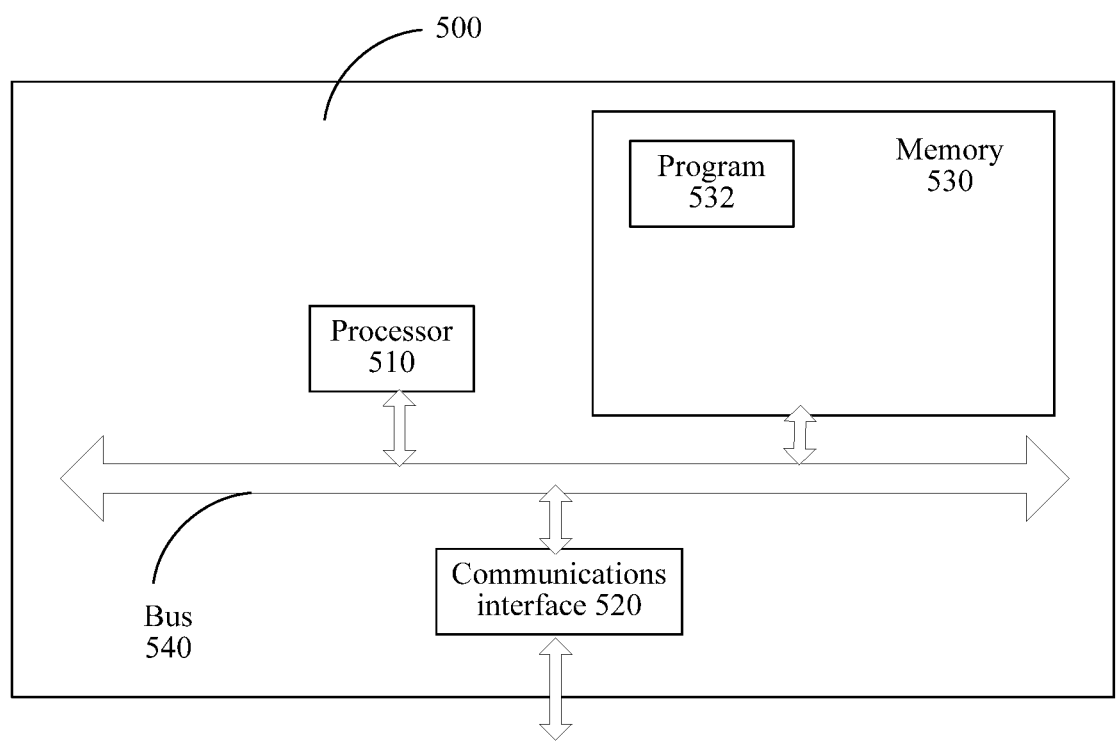
FIG. 5 is a logic block diagram of still another apparatus for determining a head movement according to an embodiment of the present application.

FIG. 5 is a schematic structural diagram of still another apparatus for determining a head movement according to an embodiment of the present application. Specific embodiments of the present application are not intended to limit specific implementation manners of apparatus 500 determining a head movement. As shown in FIG. 5, the apparatus 500 for determining a head movement may comprise:

a processor 510, a communications interface 520, a memory 530, and a communications bus 540.

The processor 510, the communications interface 520, and the memory 530 communicate with each other by using the communications bus 540.

The communications interface 520 is configured to communicate with, for example, a first communications tool, a second communications tool, and the like.

The processor 510 is configured to execute a program 532. Specifically, the processor 510 may perform relevant steps in any of the foregoing communications control method embodiments.

For example, the program 532 may comprise program code, wherein the program code comprises a computer operation instruction.

The processor 510 may be a central processing unit (CPU), an application specific integrated circuit (ASIC), or one or more integrated circuits configured to implement the embodiments of the present application.

The memory 530 is configured to store the program 532. The memory 530 may comprise a high-speed random access memory (RAM), or may further comprise a non-volatile memory, for example, at least one magnetic disk storage.

For example, in an optional implementation manner, the processor 510 may perform the following steps by performing the program 532: acquire, in response to a head movement of a human body, brain electricity detection information of the human body; and determine the head movement corresponding to the brain electricity detection information. In another optional implementation manner, the processor 510 may also perform the steps mentioned in any other embodiments described above by performing the program 532, and no further details are provided herein again.

For specific implementations of the steps in the program 532, reference may be made to corresponding descriptions of corresponding steps, modules, submodules, and units in the foregoing embodiments, and no further details are repeated herein again. It may be clearly understood by a person skilled in the art that, for the purpose of convenient and brief description, for detailed working procedures of the foregoing devices and modules, reference may be made to the description of corresponding procedures in the foregoing method embodiments, and no further details are repeated herein again.

In the foregoing embodiments of the present application, serial numbers and/or sequences of embodiments are only used for convenient description, and do not represent superior or inferior of the embodiments. In the foregoing embodiments of the present invention, the description of each embodiment may focus on certain aspects. For a part that is not described in detail in a certain embodiment, reference may be made to a related description in another embodiment.

A person of ordinary skill in the art may be aware that, in combination with the examples described in the embodiments disclosed in this specification, units and method steps may be implemented by means of electronic hardware or a combination of computer software and electronic hardware. Whether these functions are executed as hardware or software depends upon particular applications and design constraint conditions of the technical solutions. A person skilled in the art may use different methods to implement certain described functions for each particular application, but it should not be considered that the implementation goes beyond the scope of the present application.

When the functions are implemented in a form of a software functional unit and sold or used as an independent product, the functions may be stored in a non-transitory computer-readable storage medium. Based on such an understanding, the technical solutions of the present application essentially, or the part contributing to the prior art, or some of the technical solutions may be implemented in a form of a software product. The computer software product is stored in a storage medium, and comprises several instructions for instructing a computer device (which may be a personal computer, a server, a network device, or the like) to perform all or some of the steps of the methods in the embodiments of the present application. The foregoing storage medium comprises: any medium that can store program code, such as a USB flash drive, a removable hard disk, a read-only memory (ROM), a random access memory (RAM), a magnetic disk, or an optical disc.

In the apparatus, method, system embodiments of the present application, it is obviously that components (a system, a subsystem, a module, a submodule, a unit, a subunit, and the like) and steps may be decomposed, combined, and/or re-combined after decomposition. These decompositions and/or re-combinations shall be considered as equivalent solutions of the present application. Also, in the descriptions of the specific embodiments of the present application, a characteristic described and/or shown for an implementation manner may be used in one or more other implementation manners in a same or similar manner, combined with characteristics in other embodiments, or replaced the characteristics in the other embodiments.

It should be emphasized that, the term "comprise/include" used in the disclosure indicates existence of characteristics, elements, steps, or components, but does not exclude existence or addition of one or more other characteristics, elements, steps, or components.

Finally, it should be noted that, the above implementation manners are only used to describe the present application, rather than limit the present application; various alterations and modifications may be made by a person of ordinary skill in the art without departing from the spirit and scope of the present application, so all equivalent technical solutions also belong to the scope of the present application, and the scope of patent protection of the present application should be defined by the claims.

What is claimed is:

1. A method for determining a head movement, comprising:
   acquiring, in response to a head movement of a human body, brain electricity detection information of the human body;
   determining brain electricity characteristic information of the brain electricity detection information with reference to a piece of brain electricity reference information of the human body, wherein the piece of brain electricity reference information is brain electricity information of the human body acquired when the head of the human body is in a static state;
   determining the head movement corresponding to the brain electricity characteristic information;
   acquiring a control instruction corresponding to the determined head movement; and
   performing a control operation corresponding to the control instruction.

2. The method of claim 1, wherein determining the brain electricity characteristic information comprises:
   extracting information of a frequency band from the brain electricity detection information as brain electricity sample information; and
   determining, according to an amplitude of the brain electricity sample information and a reference amplitude of the piece of brain electricity reference information in the frequency band, the brain electricity characteristic information.

3. The method of claim 2, before the extracting information of a frequency band from the brain electricity detection information as brain electricity sample information, further comprising:
   determining that an amplitude of the brain electricity detection information in the frequency band is greater than a preset threshold.

4. The method of claim 2, wherein the frequency band is 0 to 5 Hz.

5. The method of claim 2, wherein the determining the head movement corresponding to the brain electricity characteristic information comprises:
   acquiring a second mapping relationship between the brain electricity characteristic information and the head movement from an external device; and
   determining, according to the second mapping relationship, the head movement corresponding to the brain electricity characteristic information.

6. The method of claim 2, wherein the determining the head movement corresponding to the brain electricity characteristic information comprises:
   establishing a second mapping relationship; and
   determining, according to the second mapping relationship, the head movement corresponding to the brain electricity characteristic information.

7. The method of claim 1, wherein the head movement comprises at least one of the following: nodding, tilting sideways, tilting up, shaking and/or rotating by the head of the human body.

8. The method of claim 1, wherein the control operation corresponding to the determined head movement comprises
   a confirmation with respect to an action when the head movement is nodding,
   a cancellation with respect to an action when the head movement is shaking, or
   controlling a volume of a playback device when the head movement is tilting to a direction.

9. An apparatus for determining a head movement, comprising:
   a brain electricity detection information acquiring module, configured to acquire, in response to a head movement of a human body, brain electricity detection information of the human body; and
   a head movement determining module, configured to determine the head movement corresponding to the brain electricity detection information,
   wherein the head movement determining module comprises:
   a brain electricity characteristic information determining submodule, configured to determine brain electricity characteristic information of the brain electricity detection information with reference to a piece of brain electricity reference information of the human body, wherein the piece of brain electricity reference information is brain electricity information of the human body acquired when the head of the human body is in a static state;
   a second head movement determining submodule, configured to determine the head movement corresponding to the brain electricity characteristic information;
   a control instruction acquiring module, configured to acquire a control instruction corresponding to the determined head movement; and
   a performing module, configured to perform a control operation corresponding to the control instruction.

10. An apparatus for determining a head movement, comprising a processor and a memory, the memory storing computer executable instructions that, when executed, cause the processor to perform operations comprising:
    acquiring, in response to a head movement of a human body, brain electricity detection information of the human body;
    determining brain electricity characteristic information of the brain electricity detection information with reference to a piece of brain electricity reference information of the human body, wherein the piece of brain electricity reference information is brain electricity information of the human body acquired when the head of the human body is in a static state;
    determining the head movement corresponding to the brain electricity characteristic information;
    acquiring a control instruction corresponding to the determined head movement; and
    performing a control operation corresponding to the control instruction.

11. The apparatus of claim 10, wherein the operations further comprise:
    extracting information of a frequency band from the brain electricity detection information as brain electricity sample information; and
    determining, according to an amplitude of the brain electricity sample information and a reference amplitude of the piece of brain electricity reference information in the frequency band, the brain electricity characteristic information.

12. The apparatus of claim 11, wherein the operations further comprise:
determining that an amplitude of the brain electricity detection information in the frequency band is greater than a preset threshold; and
according to a determined result, extracting the information of the frequency band from the brain electricity detection information.

13. The apparatus of claim 11, wherein the frequency band is 0 to 5 Hz.

14. The apparatus of claim 11, wherein the operations further comprise:
acquiring a second mapping relationship between the brain electricity characteristic information and the head movement from an external device; and
determining, according to the second mapping relationship, the head movement corresponding to the brain electricity characteristic information.

15. The apparatus of claim 11, wherein the operations further comprise:
establishing a second mapping relationship; and
determining, according to the second mapping relationship, the head movement corresponding to the brain electricity characteristic information.

16. The apparatus of claim 10, wherein the head movement comprises at least one of the following: nodding, tilting sideways, tilting up, shaking and/or rotating by the head of the human body.

17. A non-transitory computer readable storage medium comprising at least one executable instruction, which, in response to execution, causes a processor to perform operations comprising:
acquiring, in response to a head movement of a human body, brain electricity detection information of the human body;
determining brain electricity characteristic information of the brain electricity detection information with reference to a piece of brain electricity reference information of the human body, wherein the piece of brain electricity reference information is brain electricity information of the human body acquired when the head of the human body is in a static state;
determining the head movement corresponding to the brain electricity characteristic information;
acquiring a control instruction corresponding to the determined head movement; and
performing a control operation corresponding to the control instruction.

* * * * *